United States Patent [19]

Sawai et al.

[11] Patent Number: 5,260,056
[45] Date of Patent: Nov. 9, 1993

[54] COMPOSITION FOR ENHANCING BIOSYNTHESIS OF INTERFERON

[75] Inventors: Kiichi Sawai, Funabashi; Masayasu Kurono; Takahiko Mitani, both of Mie; Naohisa Ninomiya; Yoshiro Ishiwata, both of Nagoya; Syoji Yokochi, Kuwana; Kyoichi Asano, Nagoya; Kaneo Yamada, Tokyo; Masashi Taki; Takashi Meguro, both of Sagamihara; Mikio Minamitani, Tokyo; Takao Matumoto, Tokyo; Yuichi Shiokawa, Tokyo, all of Japan

[73] Assignee: Sanwa Kagaku Kenkyusho Co. Ltd., Nagoya, Japan

[21] Appl. No.: 640,750

[22] Filed: Jan. 14, 1991

Related U.S. Application Data

[62] Division of Ser. No. 433,109, Nov. 8, 1989, abandoned.

[30] Foreign Application Priority Data

Nov. 15, 1988 [JP] Japan ................. 63-286810
Nov. 27, 1988 [JP] Japan ................. 63-299202

[51] Int. Cl.$^5$ .............. A61K 37/66; A61K 59/16; A61K 31/79
[52] U.S. Cl. .................. 424/85.4; 424/650; 435/240.45; 435/240.46; 435/240.47
[58] Field of Search ............. 424/650, 85.4; 435/240.45, 240.46, 240.47

[56] References Cited

U.S. PATENT DOCUMENTS

| | | | |
|---|---|---|---|
| 4,271,084 | 6/1981 | Ishikawa et al. | 424/287 |
| 4,281,015 | 7/1981 | Ishikawa et al. | 514/492 |
| 4,296,123 | 10/1981 | Ishikawa et al. | 424/287 |
| 4,309,412 | 1/1982 | Ishikawa et al. | 424/78 |
| 4,321,273 | 3/1982 | Ishikawa et al. | 424/287 |
| 4,322,402 | 3/1982 | Ishikawa et al. | 424/78 |
| 4,889,715 | 12/1989 | Sawai et al. | 514/184 |

FOREIGN PATENT DOCUMENTS

| | | |
|---|---|---|
| 1162546 | 2/1984 | Canada . |
| 54-115324 | 9/1979 | Japan . |
| 55-167222 | 12/1980 | Japan . |
| 59-46493 | 11/1984 | Japan . |
| 60-190714 | 9/1985 | Japan . |
| 62-34725 | 7/1987 | Japan . |

*Primary Examiner*—Nathan M. Nutter
*Attorney, Agent, or Firm*—Armstrong, Westerman, Hattori, McLeland & Naughton

[57] ABSTRACT

An organic germanium compound to be effectively used for curing AIDS or making AIDS asymtomatic in various forms is expressed by the following rational formula:

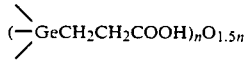

wherein n is an integer of 1 or 2 or more, is in the form of a white acicular or needle crystal, shows a solubility of 1.570/100 ml in water at 25° C. and exhibits a melting (decomposition) point of 240° C.

2 Claims, 2 Drawing Sheets

COMPOSITION FOR ENHANCING BIOSYNTHESIS OF INTERFERON

This application is a division of application Ser. No. 433,109 filed Nov. 8, 1989 and now abandoned.

BACKGROUND OF THE INVENTION

1. Field of the Invention

The present invention relates to an enhancer for biosynthesis of interferon and to a composition containing the enhancer.

2. Prior Art

Various compounds have been tested for activity as interferon inducers, and some have now been available under the trade names of Picibanil (a freeze-dried powder of Penicillin-treated *Streptococcus pyrogenes*), Krestin (a polysaccharide containing about 18–38% of protein and having an average molecular weight of about 100,000), and Maruyama Vaccine.

Additionally carcinostatics (Japanese Patent Publication No. 59-46493) and virocides (Japanese Patent Publication No. 62-34725) containing as effective ingredients dead bacterial mixtures of Pneumococcus, hemolytic Streptococcus, Staphylococcus, *Neisseria catarrhalis*, Tetracoccus, *Pseudomonas aeruginosa*, Klebsiella and *Haemophilus* influenzae have been known.

AIDS is a disease caused by human immuno-deficiency viruses (hereinafter HIV for short). Upon infection with such viruses, the helper T cell population of lymphocytes are destroyed resulting in cellular immuno-deficiency and eventually the patient succumbs opportunistic infections, Kaposi's sarcoma, etc., leading to high mortality rates.

When compared with human hepatitis virus infection, human leukemic retrovirus infection and other virus infections, the AIDS virus infections are much higher in incidence and in mortality-after-infection. To add to this, medicines now available for HIV infection are mainly inhibitor systems for the synthesis of nucleic acid, which have a grave demerit of attacking normal tissues rather than only producing a virocidal action. Thus, there is still a great demand for medicines which are safe to use and assure a high cure rate.

As reported in Japanese Patent Kokai Publication No. 52-115324, germanium polymers are effective for curing psychosis, neurosis, cacochymia, cardiopathy, anigopathy, digestive system dysfunctions, dermopathy, allergosis and renal and hepatic dysfunctions as well as various diseases in the realms of obstetrics and gynecology and pediatrics.

Additionally, Japanese Patent Kokai Publication No. 52-167222 and other publications teach that germanium polymers have an anti-DNA viral action upon influenza, Variola crystallina (herpes) and other DNA viruses.

However, nowhere in these publications is there any report on the action of organic germanium compounds as enhancers for the biosynthesis of interferon or the curing action thereof upon retroviral diseases, especially AIDS.

As is well known in the art, an organic germanium compound may be prepared as follows. Trichlorogermanium is allowed to react with acrylonitrile to obtain trichlorogermanium ethylnitrile. This is then hydrolyzed with an acid into trichlorogermanium ethyl carboxylate. Thereafter, this carboxylic acid is chlorinated with thionyl chloride into trichlorogermanium ethyl chloride which, upon exposed to water or aqueous ammonia, gives a bis-$\beta$-ethyl carboxylic acid amide germanium sesquioxide.

The thus obtained organic germanium compound is not only different in structure and physical properties from the compound according to the present invention, it has the disadvantages of differing in action from lot to lot and being unclear as to how it acts and behaves.

It is understood that some organic germanium compounds have been reported to be effective as interferon inducers, but these are still not commercially available because it is not understood how they act and behave.

Investigated and developed to overcome the demerits of these known organic germanium compounds is such a germanium polymer compound as disclosed in Japanese Patent Kokai Publication No. 54-115324. This compound is essentially common in structure to the substance according to the present invention and produces a strong effect in relatively small dosages. It is thus said to be a useful compound that satisfies various requirements for medicines. However, problems with it are that it is not only apt to undergo chemical changes during storage over an extended period of time, it is hardly absorbable in living bodies in a stable manner when administrated thereto.

Consequently, the above germanium compound is now administrated in relatively large doses, while taking its decomposition into consideration. Because the germanium compound makes use of a rare element and with resource conservation in mind, however, there is an increased demand for investigations of various preparations and compositions, with which the germanium compound can directly produce its own strong action in small amounts.

In view of the state of the art as mentioned above, the present inventors have already discovered that the pharmacological action of the organic germanium compound according to the present invention can be enhanced by the addition of a carrier for pharmaceutical preparations such as sacchardies (e.g., lactose) or high-molecular compounds (e.g., proteins), and have thus accomplished preparing a composition usable as a medicine for external application for the purpose of preventing urtication, etc. due to immunodeficiency (Japanese Patent Kokai Publication No. 60-190714). As a result of later studies, the present inventors have found that the organic germanium compound per se according to the present invention has an effect on the enhancement of biosynthesis of interferon.

SUMMARY OF THE INVENTION

The enhancer for biosynthesis of interferon according to the present invention is characterized by containing as a primary component an organic germanium polymer of the following rational formula:

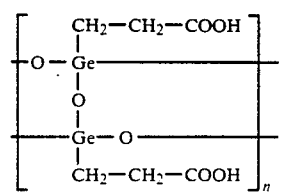

wherein n is an integer, in the form of a white acicular or needle crystal, having a solubility of 1.570/100 ml in water at 250° C. and a melting (decomposition) point of 240° C.

The composition for enhancing of interferon biosynthesis according to the present invention is characterized by comprising an organic germanium polymer of the formula:

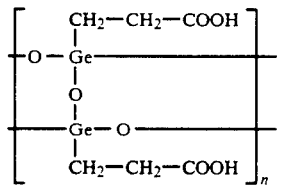

wherein n is an integer, in the form of a white acicular crystal, having a solubility of b 1.570/100 ml in water at 25° C. and a melting (decomposition) point of 240° C., and an interferon producer, said interferon producer being preferably a live or dead microbial component selected from the group consisting of influenza viruses, *Haemophilus influenzae*, hemolytic Streptococcus and Basidiomycetes or yeast cell polysaccharide.

For instance, the organic germanium compound according to the present invention may form a composition with an interferon producer such as *Broncasma berna* (a dead cell-containing antiviral preparation) and Picibanil. In this case, the composition may be stabilized by the addition of a stabilizer such as lactose. The interferon inducers, e.g., Broncasma and Picibanil may be used in the respective amounts of 5 ml/kg of weight and 10 mg/kg of weight with 50 to 80% by weight of lactose to form an interferon biosynthesis enhancer which is stable and has a high enhancing action.

The interferon producer used is preferably a live or dead microbial component selected from polynucleotides, influenza viruses, *Haemphilus influenzae*, tubercle Bacillus, hemolytic Streptococcus and Basidiomycetes or yeast cell polysacharide. However, it is desired that the use of live preparations is avoided as much as possible for patients attacked by AIDS. For such patients, the dead microbial component or a composition of the germanium compound according to the present invention with a polymeric compound, saccharides or the like should preferably used.

Lactose may be used as the saccharide. Lactose may be added in an amount of 50 to 80% by weight such that it has no influence upon the pharmacological action of the interferon inducer. This is also true of other general vehicles. By adding the interferon inducer and 50 to 80% by weight of lactose to the organic germanium compound according to the present invention, it is possible to obtain a stable, action-enhancing composition.

The polymeric carriers for pharmaceutical preparations used may include gelatin, pepsin, serum albumin, globulin, protamine, cellulosic carriers, vinylic carriers, acrylic polymer carriers, peptone, polypeptone, yeast extracts, tryptone, tryptose, dextrose and so on.

In short, the compounds according to the present invention take part in the enhancement of production of substances such as interferon in living bodies and so have a strong antiviral action therein.

The composition according to the present invention are very stable and can be continuously administered.

It is further noted that the drugs or compositions according to the present invention have the advantage of being able to be administered by an oral route and thus easier to use when compared with other drugs.

EXAMPLES

Figure 1:
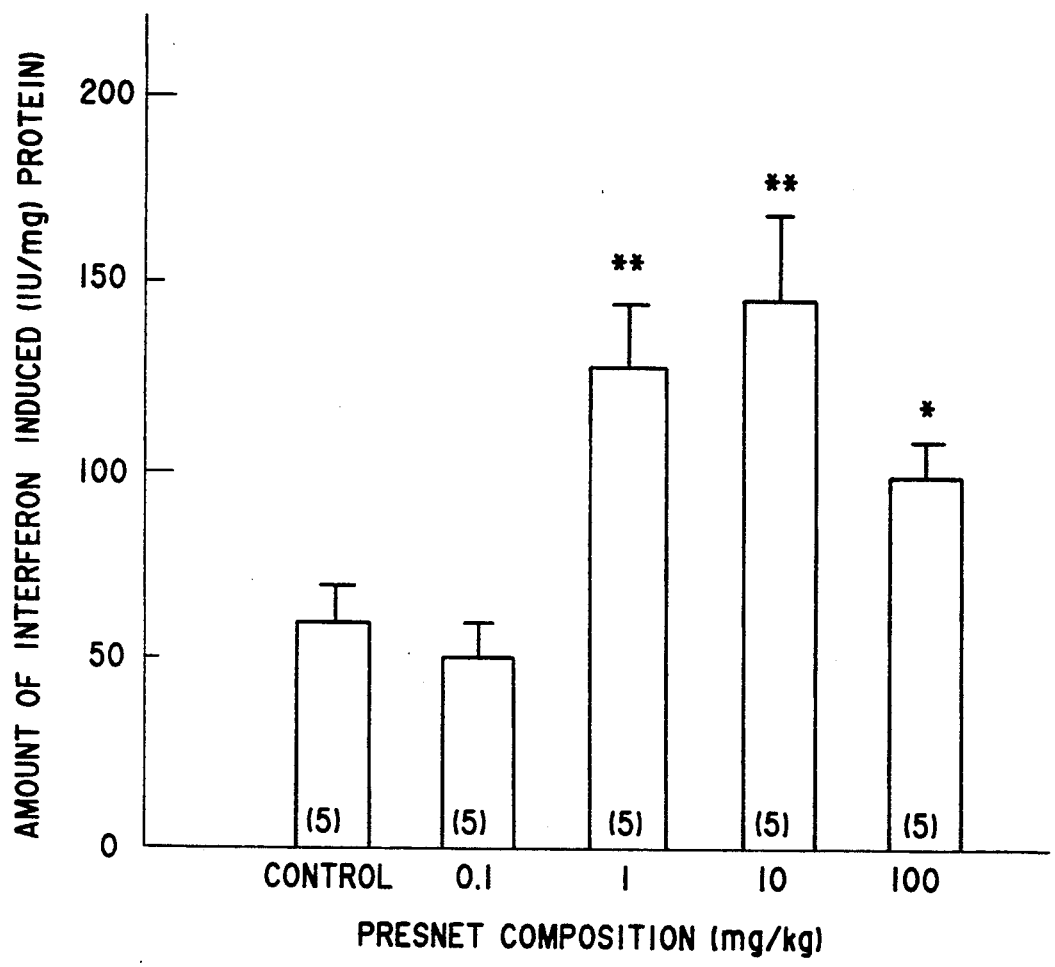
FIG. 1 is a graphical view indicating the results of experimentation on the effect of the present composition upon the enhancers of the interferon biosynthesis of mice infected with influenza viruses.

The present invention will now be explained specifically but not exclusively with reference to the following examples.

Preparation of Organic Germanium Compound

Dissolved in 2 l of ethyl alcohol are 252 g (1 mole) of 3-trichlorogermanium propionic acid, and 1.3 l of water are added under agitation to the solution. After being allowed to stand for one day, crystals are obtained by suction filtration, washed with acetone and dried under reduced pressure.

As a result, the desired organic germanium compound was obtained in the form of white acicular crystals.

Yield: 90%.

Melting (Decomposition) Point: 240° C.

Solubility at 25° C. in Water: 1.57 g/100 ml.

Pharmaceutical and Pharmacological Effects

1. Action of the Present Composition upon the Inducement of Interferon by Influenza Viruses (i) Experimental Procedures A group of five BALB/C mice were endotracheally infected with influenza viruses (A/PR/8 strains) at a dose of 8.7 PFU/mouse. Just after the infection, the composition of the present invention was orally administered to the mice at doses of 0.1 mg, 1.0 mg, 10.0 mg and 100.0 mg, calculated on the basis of the organic germanium that was the primary ingredient. After three days of the infection with influenza viruses, the lungs were removed from the mice, homogenized and centrifuged at 20000× g to obtain a supernatant. The interferon activity of the supernatant was determined in terms of L929 cytopathic inhibition by vesicular stomatitis viruses (VSV).

(ii) Experimental Results

The results are illustrated in FIG. I, from which it is noted that the composition of the present invention increases the production of interferon by a factor of 2.2, 2.5 and 1.7 at the respective doses of 1.0 mg/kg, 10.0 mg/kg and 100.0 mg/kg, calculated on the basis of the organic germanium that is the primary ingredient.

(iii) Determination of the Type of Interferon Produced and Enhanced by the Present Invention The serum of a mouse which had been infected with influenza virus and treated with the present composition, was incubated at 4° C. for one hour with an anti-mouse $\alpha/\beta$-interferon antibody, an anti-mouse $\beta$-interferon antibody and an anti-mouse $\gamma$-interferon antibody to determine the activity of interferon. As a result, it was found that the interferon activity of the serum of the mouse under examination disappeared by treatment with the anti-mouse $\alpha/\beta$-interferon antibody, but remained intact when treated with the anti-mouse β-interferon antibody and the anti-mouse γ-interferon antibody. The results suggest that the interferon of the mouse infected with influenza virus and enhanced by the present composition in terms of interferon productivity was an α-type.

2. Enhancement of Interferon Productivity of BCG Vaccine-Sensitized Mouse (i) Experimental Procedures A group of seven C57/BL/6 mice were used. Dry BCG vaccine suspended in 0.9% physiological saline was injected into the tail veins of the mice at a dose of 0.25 mg/mouse for sensitization. After ten days of the sensitization, they were orally administered the composition of the present at dosages of 0.1, 1, 10 and 100 mg/kg calculated on the basis of the organic germanium. On the day following the final administration (14 days after sensitization), BCG was intravenously injected at a dose of 0.1 mg/mouse. Three hours later, blood was collected to determine the interferon activity of the separated serum.

(ii) Results of Experimentation

Figure 2:
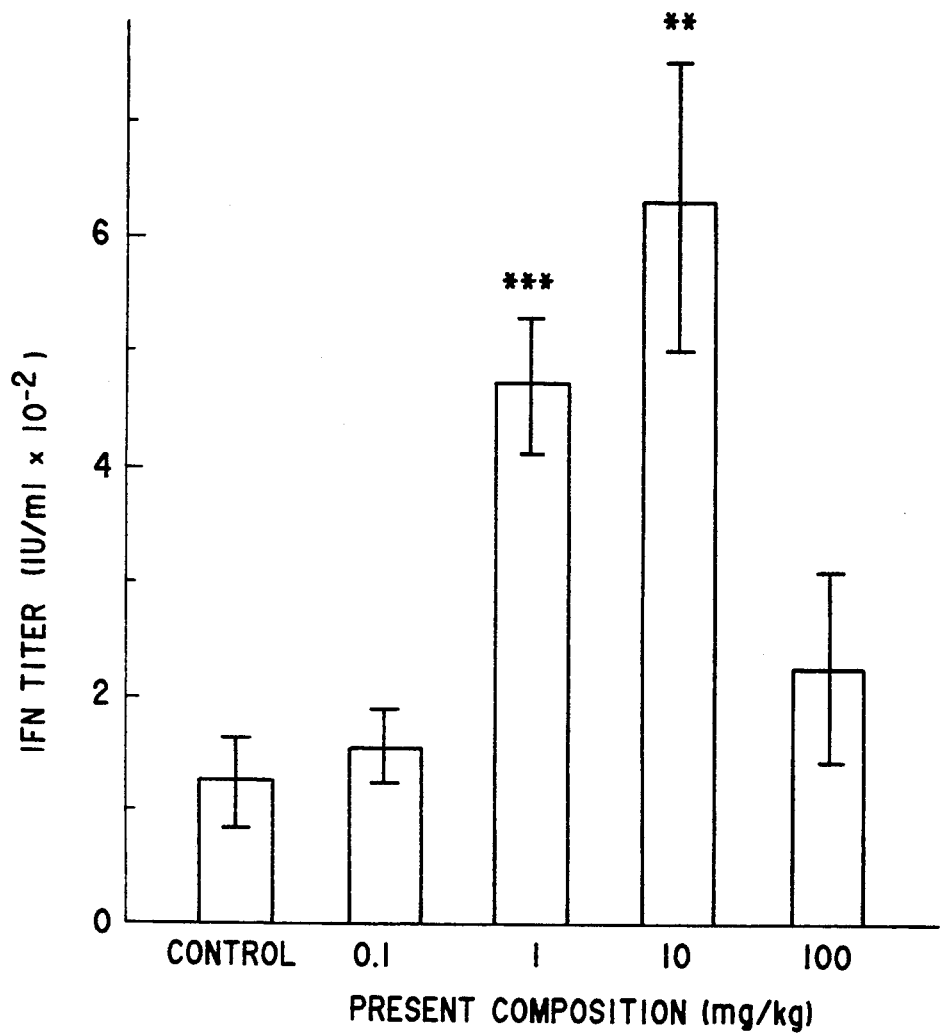
FIG. 2 is a graphical view showing the results of experimentation on the effect of the present composition upon the enhancement of the production of interferon of BCG-infected mice.

The experimental results are graphically illustrated in FIG. 2, from which it is found that the composition according to the present invention significantly enhances the interferon production of the BCG-sensitized mouse and increases the production of interferon by a factor of 3.7 and 5.0 at the respective doses of 1.0 mg/kg and 10.0 mg/kg, calculated on the basis of the organic germanium, over a control group.

(iii) Determination of the Type of Interferon of BCG-Sensitized Mouse Enhanced in Terms of its Production by the Present Composition The serum of a BCG-sensitized mouse administered with the present composition was dialyzed with 0.1 mg of an lysin-HCl buffer of pH 2.0 for 24 hours to determine its interferon activity.

As a result, the interferon of the serum of the BCG-sensitized mouse which had been administered the present composition was deactivated. On the other hand, standard α/β-interferon treated in a similar manner as mentioned above showed a barely 22% decrease of activity.

BCG-sensitized mice are known to produce γ-interferon. Thus, it was revealed that the interferon of the BCG-sensitized mouse enhanced in terms of its production was a γ-type.

2. Stabilization of Commercially Available Preparations

Tests were made on the effect of the present composition upon the enhancement of the inducement of interferon in commercially available preparations. As in interferon inducer, use was made of an antiviral preparation containing as an effective ingredient different types of dead bacteria (*Broncasma berna*, Japanese Patent Kokai Publication No. 62-34725).

(i) Experimental Procedures

A group of five BALB/C mice were intraperitoneally injected with 5 ml/kg of *Broncasma berna*, immediately after which the present composition was orally administered thereto at a dose of 1.0 mg/kg calculated on the basis of the organic germanium. After 20 hours of the administration, blood was collected from each mouse to determine the interferon activity of the separated serum.

(ii) Results of Experimentation

Consequently, it was noted that, as shown in Table 1, the present composition successfully increases the inducement of interferon of Broncasma berna by a factor of about 3.

TABLE 1

|  | Interferon Activity (IU/ml) |
| --- | --- |
| Control | not detected |
| Broncasma berna | 110 |
| Broncasma berna + Present Composition | 320 |

3. Results of Clinical Test

Six HIV-infected subjects, four positive and two negatives, (all being male haemaphiliacs between the ages of 6 and 22, asymptomatic carriers) were administered the preparation of the present invention (to be described later) over a period of seven months (at a dose of 60 mg/day calculated on the basis of the organic germanium compound, but at a dose of 40 mg/day for under ten years of age) to make immunological studies of the number of lymphocytes, OKT4, OKT4/8 and so on. In the meantime, virus markers such as HIV, HIV antigens and HIV antibodies were measured with clinical observations. There was virtually no difference in the number of lymphocytes, for instance, $2370\pm311/\mu l$ before administration and $2349\pm312/\mu l$ after six months of administration. The number of OKT4 increased from $463\pm64 /\mu l$ before administration to $549\pm89/\mu l$ after two months of administration and $629\pm97 /\mu l$ after six months of administration. The number of OKT8 decreased slightly from $1303\pm174/\mu l$ before administration to $1154\pm153/\mu l$ after six months of administration.

The number of OKT4/8 showed a gradually increasing tendency, that is, from $0.35\pm0.03$ before administration to $0.42\pm0.02$ after one month of administration of $0.51\pm0.05$ after six months of administration.

The separation of viruses in blood was carried out by the CDC (Center for Disease Control), while HIV antigens were measured on a daily basis by the Western Blotting method with P24.

Of the four HIV-positive subjects, two suffered from no change by the six-moth administration of the present compound, but the other two showed no sign of HIV at all (Table 2).

On the other hand, there was no clinically noticeable side-effects and two subjects had a good appetite and gained weight.

TABLE 2

Changes of Virus Markers of HIV-Positive Subjects
(Results Obtained as of October, 1988)

|  |  | 0 week | 6 months | 7 months |
| --- | --- | --- | --- | --- |
| Subject A | HIV Separation | + | − | − |

TABLE 2-continued

Changes of Virus Markers of HIV-Positive Subjects
(Results Obtained as of October, 1988)

|  |  |  |  |  |  |  |
|---|---|---|---|---|---|---|
|  | HIV Antigen | − |  | − |  | − |
|  | HIV Antibody | + |  | + |  | + |
|  |  | −5 weeks | 0 week | 2 weeks | 6 months | 7 months |
| Subject B | HIV Separation | + | + | + | − | − |
|  | HIV Antigen | + | + | + | + | + |
|  | HIV Antibody | + | + | + | + | + |

Referring to the above two subjects, diagnosed as HIV-positive as of Oct., 1988, HIV was killed (HIV-negative) after and 12 months of the initial administration. In all the cases, HIV was eventually killed (i.e., HIV-negative). Such an effective action encouraged an additional four subjects to receive treatment. Referring to two of these subjects, they became HIV-negative after 4 and 7 months after administration. Later, candidates increased steadily and reached twelve as of September, 1989.

Referring to the first-mentioned four subjects, HIV was killed after 6 months at the earliest and 12 months at the latest. From the results of the later tests, it was noted that HIV was killed after 4 months of administration.

4 Examples of Preparations

| (i) Nebulizer | |
|---|---|
| *Broncasma berna* | 10 ml |
| Solvent obtained by adding and dissolving the present organic germanium compound into a 4% solution of serum albumin at a concentration of 1.0% | 90 ml |

The above ingredients are mixed together into a nebulizer preparation.

| (ii) Granules | |
|---|---|
| Prescription | |
| Kresin | 1 g |
| Present organic germanium compound | 20 mg |
| Hydroxypropyl cellulose | 75 mg |
| Magnesium stearate | 7.5 mg |
| Lactose | suitable quantity |
|  | 1.5 g per chartula |

According to the above prescription, the organic germanium compound and lactose are mixed and melted together under wet conditions, followed by drying and granulation. The product is mixed with the rest into a capsule in the ordinary manner.

| (iii) Capsule 1 | |
|---|---|
| Prescription | |
| Krestin | 300 mg |
| Present organic germanium compound | 10 mg |
| Hydroxypropy celluose | 15 mg |
| Magnesium stearate | 3 mg |
| Lactose | suitable quantity |
|  | 380 mg per capsule |

According to the above prescription, the organic germanium compound and lactose are mixed and melted together under wet conditions, followed by drying and granulation. The product is mixed with the rest into a capsule in the ordinary manner.

| (iv) Capsule 2 | |
|---|---|
| Prescription | |
| Present organic germanium compound | 10 mg |
| Lactose | 165.5 mg |
| HPC-L (hydroxypropyl cellulose) | 2.7 mg |
| Magnesium stearate | 1.8 mg |
|  | 180 mg per capsule |

5. Example of Preparation Used Exclusively with Interferon Inducer

| Tablet | |
|---|---|
| Prescription | |
| Composition obtained by adding and dissolving the organic germanium compound into an 1% aqueous solution of pepsin at a concentration of 1%. followed by freeze-drying | 60 mg |
| Carboxymethyl cellulose calcium | 7 mg |
| Light silicic anhydride | 1 mg |
| Magnesium stearate | 7 mg |
| Lactose | suitable quantity |
|  | 165 mg per tablet |

This is an example of a preparation which is to be administered in combination with an interferon inducer in the form of an injection.

What is claimed is

1. A composition for enhancing the biosynthesis of interferon in living bodies comprising a) an interferon inducer selected from the group consisting of Broncasma berna, influenza viruses, Hemophilus influenza, hemolytic Streptococcus and Basidiomycetes and yeast cell polysaccharide; and b) an organogermanium polymer having the structural unit;

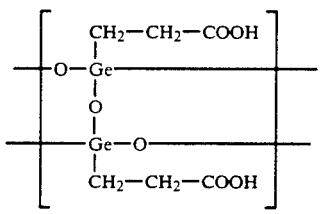

said polymer being in the form of white needle-shaped crystals which melt with decomposition at 240° C. and which have a solubility of 1.570 g per 100 ml of water at 25° C.

2. A composition according to claim 1, wherein the interferon inducer is Broncasma berna.

* * * * *